US012593879B1

(12) United States Patent
Eadicicco

(10) Patent No.: US 12,593,879 B1
(45) Date of Patent: Apr. 7, 2026

(54) MOTION-SENSING AND TRACKING OUTFIT FOR USE WHILE EXERCISING

(71) Applicant: Shannon Eadicicco, Bayville, NJ (US)

(72) Inventor: Shannon Eadicicco, Bayville, NJ (US)

( * ) Notice: Subject to any disclaimer, the term of this patent is extended or adjusted under 35 U.S.C. 154(b) by 805 days.

(21) Appl. No.: 17/982,577

(22) Filed: Nov. 8, 2022

(51) Int. Cl.
| | |
|---|---|
| *A61B 5/00* | (2006.01) |
| *A41D 1/00* | (2018.01) |
| *A41D 13/12* | (2006.01) |
| *A61B 5/11* | (2006.01) |
| *G01P 15/18* | (2013.01) |
| *A63B 24/00* | (2006.01) |

(52) U.S. Cl.
CPC ......... *A41D 1/002* (2013.01); *A41D 13/1281* (2013.01); *A61B 5/11* (2013.01); *A61B 5/6804* (2013.01); *G01P 15/18* (2013.01); *A63B 24/0062* (2013.01)

(58) Field of Classification Search
CPC ...... A41D 1/002; A41D 13/1281; A61B 5/11; A61B 5/6804; G01P 15/18; A63B 24/0062
See application file for complete search history.

(56) References Cited

U.S. PATENT DOCUMENTS

| | | | | |
|---|---|---|---|---|
| 7,602,301 B1* | 10/2009 | Stirling | ................ | A61B 5/1124 |
| | | | | 340/573.7 |
| D901,834 S | 11/2020 | Frouin | | |
| 11,071,498 B2* | 7/2021 | Connor | ................ | A61B 5/6805 |

| | | | | |
|---|---|---|---|---|
| 11,179,601 B2 | 11/2021 | Wiebe | | |
| 11,210,834 B1* | 12/2021 | Chamdani | ............... | G06T 13/40 |
| 11,497,964 B1* | 11/2022 | Hunter | ................. | A63B 53/005 |
| 11,583,011 B2* | 2/2023 | Mazzarolo | ........... | A41D 13/018 |
| 11,589,782 B2* | 2/2023 | Demircan | ............ | A61B 5/4585 |
| 11,975,195 B1* | 5/2024 | Heldman | ............. | A61B 5/7264 |
| 2002/0111777 A1* | 8/2002 | David | .................... | A61B 5/252 |
| | | | | 702/189 |
| 2008/0258921 A1* | 10/2008 | Woo | ......................... | G10H 1/40 |
| | | | | 482/8 |
| 2011/0166491 A1* | 7/2011 | Sankai | ............... | A41D 13/1281 |
| | | | | 601/84 |
| 2012/0086550 A1* | 4/2012 | LeBlanc | .................. | G07C 9/37 |
| | | | | 340/5.82 |
| 2012/0188158 A1* | 7/2012 | Tan | ......................... | G06F 3/015 |
| | | | | 345/156 |
| 2012/0271143 A1* | 10/2012 | Aragones | ................. | G09B 5/02 |
| | | | | 600/595 |
| 2012/0330109 A1* | 12/2012 | Tran | ................... | A61B 5/14532 |
| | | | | 600/509 |

(Continued)

FOREIGN PATENT DOCUMENTS

WO        2022055765        3/2022

*Primary Examiner* — May A Abouelela
(74) *Attorney, Agent, or Firm* — Kyle A. Fletcher, Esq.

(57)        ABSTRACT

The motion-sensing and tracking outfit for use while exercising is a garment. The motion-sensing and tracking outfit for use while exercising is adapted for use with a patient. The patient wears the motion-sensing and tracking outfit for use while exercising. The motion-sensing and tracking outfit for use while exercising monitors the motion of the patient during exercise. The motion-sensing and tracking outfit for use while exercising analyses the movement of the patient to determine whether the patient is using the proper form for the exercise. The motion-sensing and tracking outfit for use while exercising comprises a therapeutic structure.

12 Claims, 5 Drawing Sheets

(56) References Cited

U.S. PATENT DOCUMENTS

| | | | | |
|---|---|---|---|---|
| 2014/0012161 | A1* | 1/2014 | Ross, Jr. | A41D 1/002 |
| | | | | 600/595 |
| 2014/0135593 | A1* | 5/2014 | Jayalth | G09B 19/0038 |
| | | | | 600/301 |
| 2014/0135960 | A1* | 5/2014 | Choi | A61B 5/0205 |
| | | | | 700/91 |
| 2014/0199672 | A1* | 7/2014 | Davidson | A63B 21/0058 |
| | | | | 434/247 |
| 2014/0266160 | A1* | 9/2014 | Coza | A63B 47/008 |
| | | | | 324/207.11 |
| 2015/0250420 | A1* | 9/2015 | Longinotti-Buitoni | |
| | | | | A61B 5/1135 |
| | | | | 600/534 |
| 2015/0366504 | A1* | 12/2015 | Connor | A61B 5/6804 |
| | | | | 600/301 |
| 2016/0338621 | A1* | 11/2016 | Kanchan | A61B 5/11 |
| 2016/0338644 | A1* | 11/2016 | Connor | A61B 5/1126 |
| 2017/0189752 | A1* | 7/2017 | Mohrman | A61B 5/4866 |
| 2017/0258390 | A1* | 9/2017 | Howard | A61B 5/4803 |
| 2018/0024622 | A1 | 1/2018 | Cobanoglu | |
| 2018/0093121 | A1* | 4/2018 | Matsuura | G09B 19/0038 |
| 2018/0116560 | A1* | 5/2018 | Quinn | A61B 5/02055 |
| 2018/0174420 | A1* | 6/2018 | Clark | G08B 25/10 |
| 2018/0184735 | A1* | 7/2018 | Longinotti-Buitoni | |
| | | | | A61B 5/282 |
| 2019/0029594 | A1 | 1/2019 | Jiang | |
| 2019/0134454 | A1* | 5/2019 | Mahoney | A63F 13/24 |
| 2019/0223525 | A1* | 7/2019 | Mazzarolo | A41D 1/002 |
| 2019/0283247 | A1* | 9/2019 | Chang | A61B 5/1121 |
| 2020/0029899 | A1* | 1/2020 | Bogdanovich | A61B 5/746 |
| 2020/0029900 | A1* | 1/2020 | Bogdanovich | A61B 5/6804 |
| 2020/0129811 | A1* | 4/2020 | Kruger | A61B 5/0022 |
| 2020/0157713 | A1* | 5/2020 | Nakajima | H01B 13/008 |
| 2020/0163621 | A1* | 5/2020 | Connor | A61B 5/389 |
| 2020/0372825 | A1 | 11/2020 | Ghassemi | |
| 2021/0084997 | A1 | 3/2021 | Zealand | |
| 2021/0195732 | A1* | 6/2021 | Longinotti-Buitoni | |
| | | | | H05K 3/361 |
| 2021/0252280 | A1* | 8/2021 | Stathis | A61N 1/36034 |
| 2021/0315490 | A1* | 10/2021 | Connor | A61B 5/1126 |
| 2021/0345962 | A1* | 11/2021 | Fong | A61B 5/1121 |
| 2022/0000424 | A1* | 1/2022 | Nebuya | A61B 5/113 |
| 2022/0047181 | A1* | 2/2022 | Demircan | A61B 5/0024 |
| 2022/0054041 | A1* | 2/2022 | Menon | G06N 20/00 |
| 2022/0061412 | A1* | 3/2022 | Culver, II | A41D 13/02 |
| 2022/0079521 | A1 | 3/2022 | Grena | |
| 2022/0117553 | A1* | 4/2022 | Chahine | A61B 5/0535 |
| 2022/0296129 | A1* | 9/2022 | Dodemont | A61B 5/053 |
| 2023/0000423 | A1* | 1/2023 | Sarkar | A61B 5/4803 |
| 2023/0001031 | A1* | 1/2023 | Curry | A41D 27/20 |
| 2023/0024285 | A1* | 1/2023 | Hearsch | A41D 13/1236 |
| 2023/0047341 | A1* | 2/2023 | Pedley | A61B 5/296 |
| 2023/0089750 | A1* | 3/2023 | Young | A61B 5/6804 |
| | | | | 600/595 |
| 2023/0134637 | A1* | 5/2023 | Brodie | A61N 1/36031 |
| | | | | 607/48 |
| 2024/0172963 | A1* | 5/2024 | Carbo, Jr. | A61B 5/01 |

* cited by examiner

100

104

102

144

151

103

102

143

111

111

103

1

MOTION-SENSING AND TRACKING OUTFIT FOR USE WHILE EXERCISING

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of sensors adapted to be attached to or worn on the body surface. (A61B5/6801)

SUMMARY OF INVENTION

The motion-sensing and tracking outfit for use while exercising is a garment. The motion-sensing and tracking outfit for use while exercising is adapted for use with a patient. The patient wears the motion-sensing and tracking outfit for use while exercising. The motion-sensing and tracking outfit for use while exercising monitors the motion of the patient during exercise. The motion-sensing and tracking outfit for use while exercising analyses the movement of the patient to determine whether the patient is using the proper form for the exercise. The motion-sensing and tracking outfit for use while exercising comprises a therapeutic structure.

These together with additional objects, features and advantages of the motion-sensing and tracking outfit for use while exercising will be readily apparent to those of ordinary skill in the art upon reading the following detailed description of the presently preferred, but nonetheless illustrative, embodiments when taken in conjunction with the accompanying drawings.

In this respect, before explaining the current embodiments of the motion-sensing and tracking outfit for use while exercising in detail, it is to be understood that the motion-sensing and tracking outfit for use while exercising is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the motion-sensing and tracking outfit for use while exercising.

It is therefore important that the claims be regarded as including such equivalent construction insofar as they do not depart from the spirit and scope of the motion-sensing and tracking outfit for use while exercising. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

Figure 1:
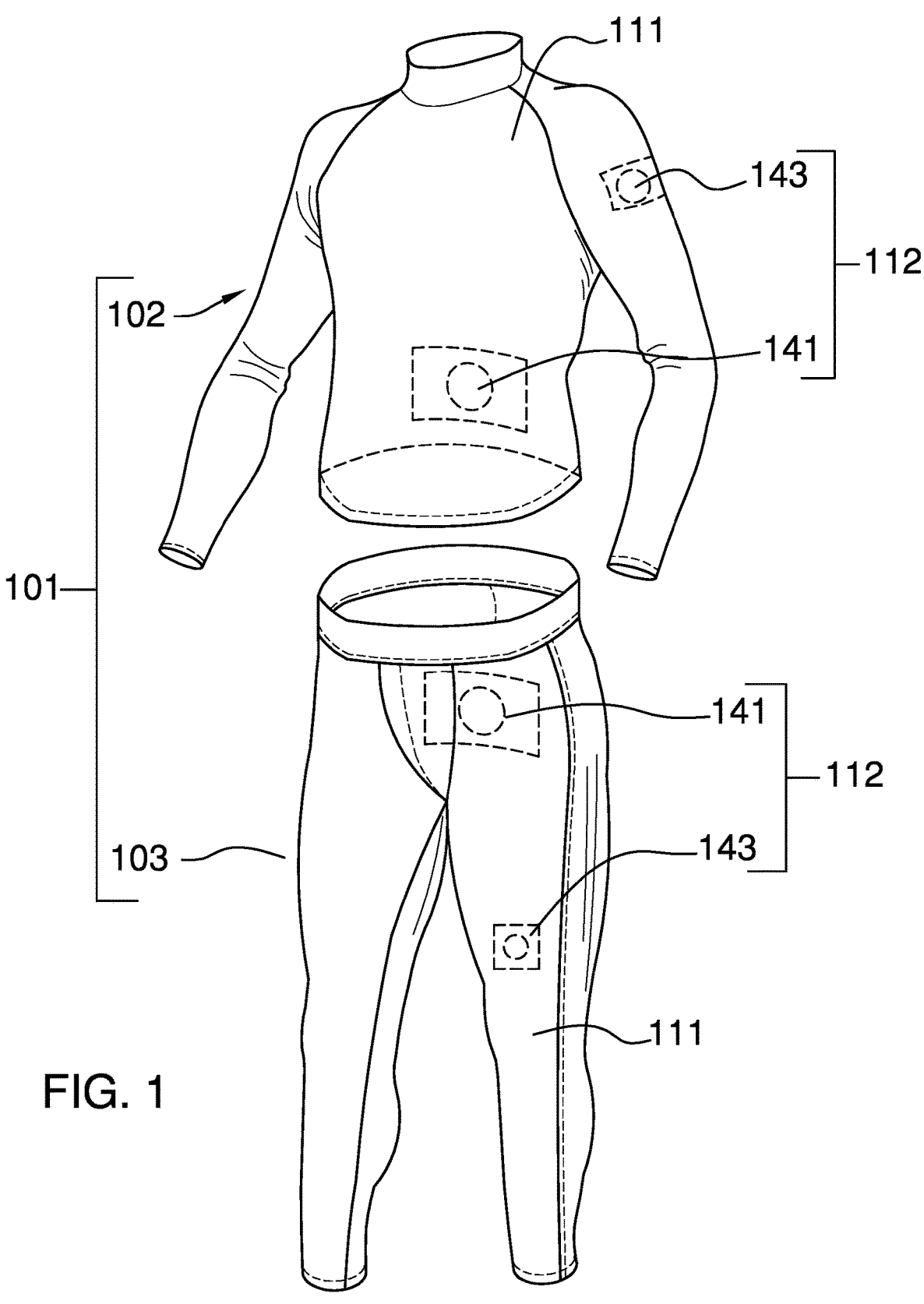

FIG. 1 is a perspective view of an embodiment of the disclosure.

Figure 2:
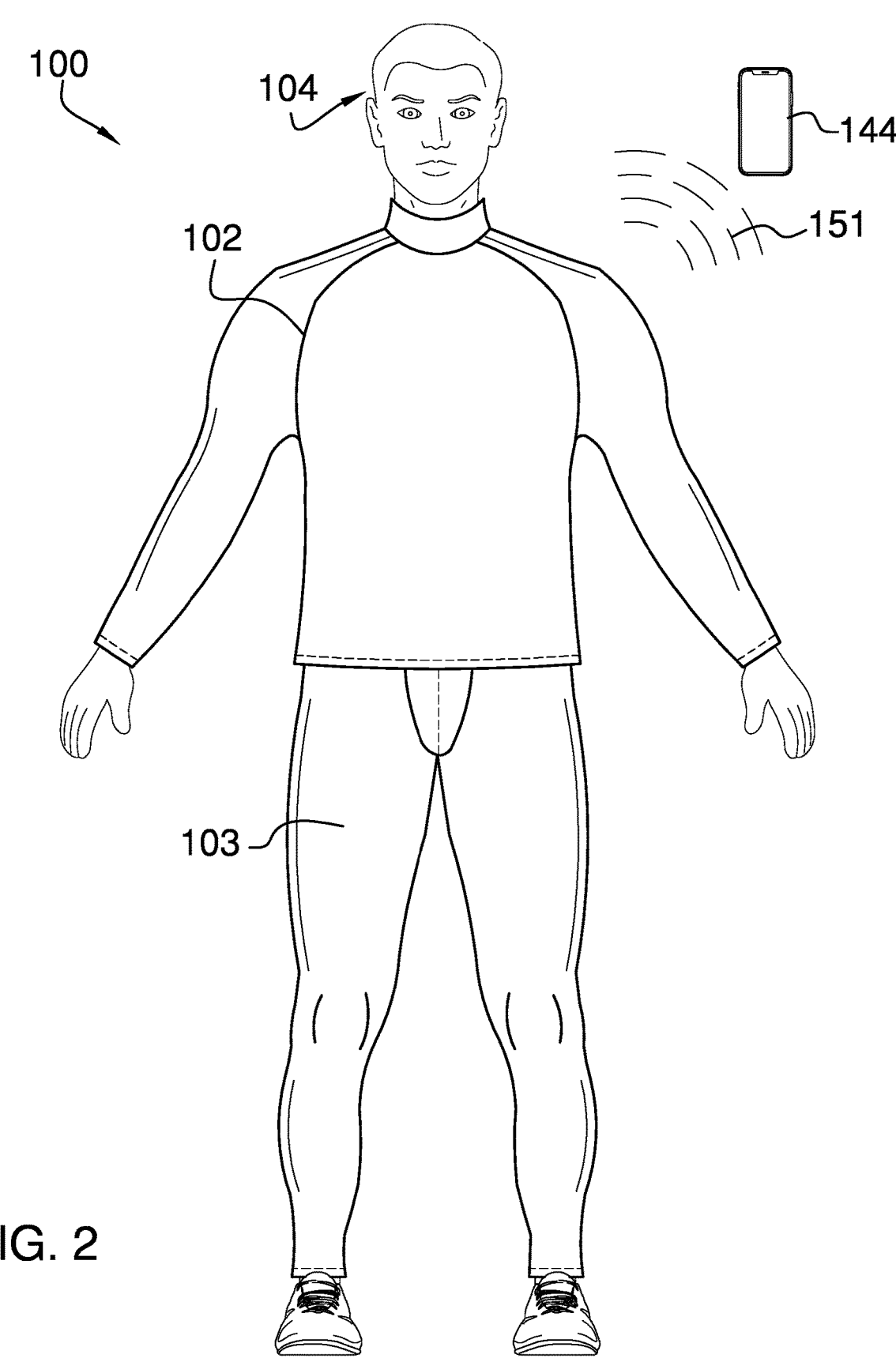

FIG. 2 is a front view of an embodiment of the disclosure.

Figure 3:
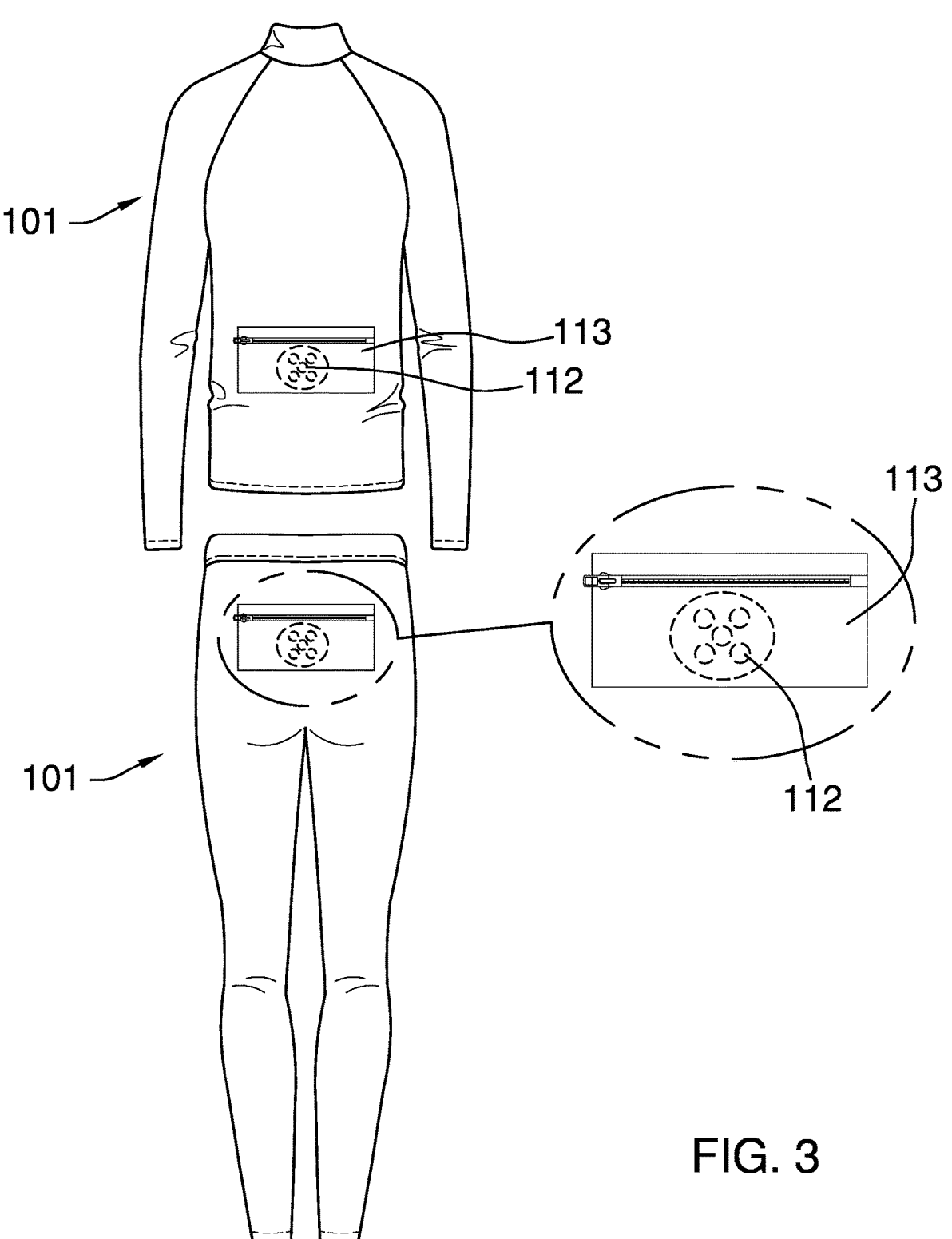

FIG. 3 is a rear view of an embodiment of the disclosure.

Figure 4:
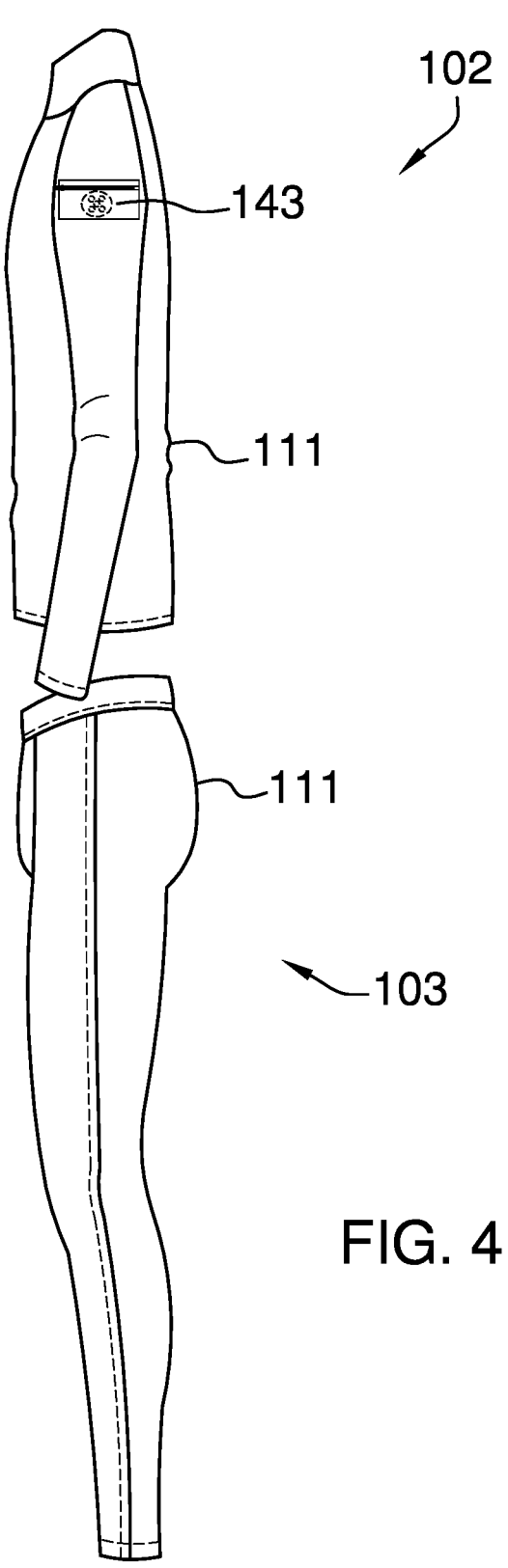

FIG. 4 is a side view of an embodiment of the disclosure.

Figure 5:
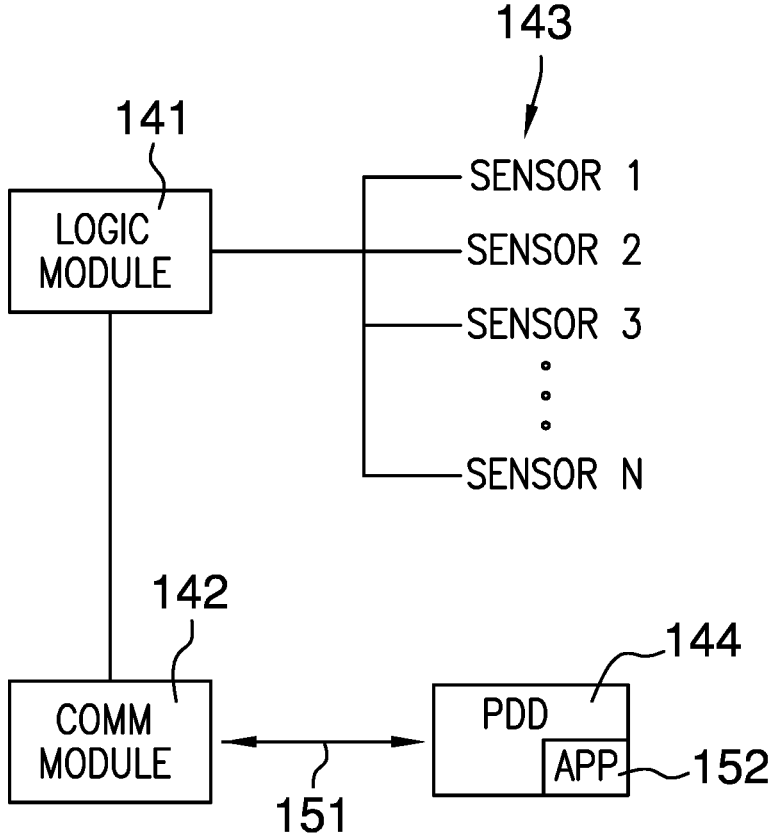

FIG. 5 is a schematic view of an embodiment of the disclosure.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Detailed reference will now be made to one or more potential embodiments of the disclosure, which are illustrated in FIGS. 1 through 5.

The motion-sensing and tracking outfit for use while exercising 100 (hereinafter invention) is a garment. The invention 100 is adapted for use with a patient 104. The patient 104 wears the invention 100. The invention 100 monitors the motion of the patient 104 during exercise. The invention analyses the movement of the patient 104 to determine whether the patient 104 is using the proper form for the exercise. The invention 100 comprises a therapeutic structure 101. The patient 104 is the individual designated to wear the invention 100.

In the first potential embodiment of the disclosure, the therapeutic structure 101 comprises a superior therapeutic structure 102. The superior therapeutic structure 102 is an instantiation of the invention 100. The superior therapeutic structure 102 is worn by the patient 104 while exercising. The superior therapeutic structure 102 encloses the torso and arms of the patient 104.

In a second potential embodiment of the disclosure, the therapeutic structure 101 comprises an inferior therapeutic 9 structure 103. The inferior therapeutic structure 103 is an instantiation of the invention 100. The inferior therapeutic structure 103 is worn by the patient 104 while exercising. The inferior therapeutic structure 103 encloses the hips, pelvis, and legs of the patient 104.

The therapeutic structure 101 is a garment. The therapeutic structure 101 is worn by the patient 104. The therapeutic structure 101 forms a tight fit on the patient 104. The therapeutic structure 101 senses changes in the position of the patient 104. Specifically, the therapeutic structure 101 measures the change of position of one or more specific locations of the patient 104. The therapeutic structure 101 measures the change of position of the one or more specific locations of the patient 104 while the patient 104 is exercising.

The therapeutic structure 101 analyzes the measured change of position of each measured location of the body of the patient 104. The therapeutic structure 101 compares the change of any first measured location of the patient 104 relative to the change of position of any second measured location of the patient 104 to determine the motion of the first measured location relative to the second measured location. The therapeutic structure 101 analyzes the measured change of position of any measured first location of the patient 104 to the measured position of each of the other measured locations of the patient 104. The therapeutic structure 101 compares the relative change between any two measured locations of the patient 104 to determine the form the patient 104 is using during the exercise. The therapeutic structure 101 compares the measured exercise form of the patient 104 to the form that is recommended for the exercise. The therapeutic structure 101 provides a summary of the differences between the patient's exercise form and the recommended exercise form to the patient 104.

The therapeutic structure 101 comprises a base garment 111, a base circuit 112, and a zippered pocket 113. The zippered pocket 113 attaches to the base garment 111. The zippered pocket 113 contains a portion of the base circuit 112.

The base garment 111 forms the garment that is worn by the patient 104. The base garment 111 is a compression garment. The compression garment is defined elsewhere in this disclosure. The compression provided by the base garment 111 maintains each inertial sensor selected form the plurality of inertial sensors in a fixed position relative to the patient 104.

The zippered pocket 113 is a pocket that is formed on the exterior surface of the base garment 111 that is worn by the patient 104. The zippered pocket 113 encloses a portion of the base circuit 112. The zippered pocket 113 further comprises a zipper. The zipper of the zippered pocket 113 encloses the portion of the base circuit 112 stored in the zippered pocket 113.

The base circuit 112 is an electric circuit. The base circuit 112 senses changes in the position of the patient 104. The base circuit 112 measures the change of position of the one or more specific locations of the patient 104. The base circuit measures the change of position of the one or more specific locations of the patient 104 while the patient 104 is exercising.

The base circuit 112 analyzes the measured change of position of each measured location of the body of the patient 104. The base circuit 112 compares the change of any first measured location of the patient 104 relative to the change of position of any second measured location of the patient 104 to determine the motion of the first measured location relative to the second measured location. The base circuit 112 analyzes the measured change of position of any measured first location of the patient 104 to the measured position of each of the other measured locations of the patient 104. The base circuit 112 compares the relative change between any two measured locations of the patient 104 to determine the form the patient 104 is using during the exercise. The base circuit 112 compares the measured exercise form of the patient 104 to the form that is recommended for the exercise. The base circuit 112 provides the summary of the differences between the patient's exercise form 12 and the recommended exercise form to the patient 104.

The base circuit 112 comprises a logic module 141, a communication module 142, a plurality of inertial sensors 143, and a personal data device 144. The logic module 141, the communication module 142, and the plurality of inertial sensors 143 are electrically interconnected. The communication module 142 forms a communication link with the personal data device 144. The communication module 142 further comprises a wireless communication link 151. The personal data device 144 further comprises an application 152.

The logic module 141 is a programmable electronic device that is used to manage, regulate, and operate the base circuit 112. The communication module 142 is a wireless electronic communication device that allows the logic module 141 to wirelessly communicate with a personal data device 144. The communication module 142 prepares a direct messaging facility that is transmitted over the wireless communication link 151 to the personal data device 144. The message contained in the direct messaging facility contains the inertial readings from the plurality of inertial sensors 143 that have been processed by the logic module 141. In the first potential embodiment of the disclosure, the communication module 142 supports a communication protocol selected from the group consisting of a WiFi™ protocol or a Bluetooth™ protocol.

The logic module 141 electrically connects with the communication module 142. The logic module 141 electrically connects with each inertial sensor selected form the plurality of inertial sensors 143. The logic module 141 monitors the motion of each selected inertial sensor. The logic module 141 prepares the direct message facility containing an analysis of the relative motions between any first inertial sensor selected form the plurality of inertial sensors 143 and any second inertial sensor selected form the plurality of inertial sensors 143. The logic module 141 transmits the direct message facility to the communication module 142 which retransmits the received direct message facility to the personal data device 144.

The personal data device 144 is a programmable electrical device. The personal data device 144 further comprises an application 152. The personal data device 144 provides data management and communication services through one or more functions referred to as an application 152. The application 152 is a set of logical operating instructions that are performed by the personal data device 144. The addition of an application 152 will provide increased functionality for the personal data device 144. This disclosure assumes that an application 152 exists for the purpose of interacting with the patient 104. The application 152 of the personal data device forms an interface between the base circuit 112 and a patient 104 using the invention 100. The personal data device 144 transmits operating instructions over the wireless communication link 151 to the base circuit 112. The communication module 142 receives the transmitted operating instructions and relays the received operating instructions to the logic module 141.

In each potential embodiment of the disclosure, the application 152 receives the direct message facility from the logic module 141. The application 152 compares the received relative motions between the plurality of inertial sensors 143 against the motions recommended for each exercise. The application 152 provides the summary of the differences between the patient's exercise form and the recommended exercise form to the patient 104 through the personal data device 144.

Each inertial sensor selected form the plurality of inertial sensors 143 is a sensor that is mounted on the base garment

5

111. The compression provided by the base garment 111 maintains each selected inertial sensor in a fixed position relative to the patient 104. Each selected inertial sensor senses changes in the position of the selected inertial sensor relative to the force of gravity. Each selected inertial sensor converts the sensed change of position into an electric signal. Each selected inertial sensor transmits the converted electric signal to the logic module 141 for further processing. In the first potential embodiment of the disclosure, each inertial sensor selected form the plurality of inertial sensors 143 is a triple axis acceleration sensor.

The following definitions were used in this disclosure:

Abdomen: As used in this disclosure, the abdomen refers to the portion of the torso between the bottom of the rib cage and the hips of the person.

Anterior: As used in this disclosure, anterior is a term that is used to refer to the front side or direction of a structure. When comparing two objects, the anterior object is the object that is closer to the front of the structure.

Application or App: As used in this disclosure, an application or app is a self-contained piece of software that is especially designed or downloaded for use with a personal data device.

Bluetooth™: As used in this disclosure, Bluetooth™ is a standardized communication protocol that is used to wirelessly interconnect electronic devices.

Channel: As used in this disclosure, a channel is a previously determined frequency of electromagnetic radiation that is used for wireless communication. Wireless communication structures often designate a plurality of channels which allows users to "change the channel" when a previously specified channel is experiencing some form of interference.

Communication Link: As used in this disclosure, a communication link refers to the structured exchange of data between two objects.

Composite Textile: As used in this disclosure, a composite textile is a multilayer fabric made of two or more joined layers of textile or sheeting materials.

Compress: In this disclosure, compress means to apply a force to force a fixed mass of material into a smaller volume of space.

Compression Garment: As used in this disclosure, a compression garment is made from an elastic fabric. The compression garment is worn by a patient. The compression garment is formed from one or more tubular structures. The one or more tubular structures form sleeves that enclose the body of the patient. The volume of the interior of the compression garment is less than the volume of the body regions of the patient that are enclosed by the compression garment. When worn, the compression garment applies a force against the patient as the compression garment attempts to return to its relaxed shape.

Elastic: As used in this disclosure, an elastic is a material or object that deforms when a force is applied to it and that is able to return to its relaxed shape after the force is removed. A material that exhibits these qualities is also referred to as an elastomeric material. A material that does not exhibit these qualities is referred to as inelastic or an inelastic material.

Elastic Textile: As used in this disclosure, an elastic textile is a textile that contains elastic yarns as some of the yarns that make up the textile. An elastic textile is constructed such that the elastic textile will stretch when a force is applied and will return to its original shape when after the force is removed.

Elevation: As used in this disclosure, elevation refers to the span of the distance in the superior direction between a specified horizontal surface and a reference horizontal surface. Unless the context of the disclosure suggests otherwise, the specified horizontal surface is the supporting surface the potential embodiment of the disclosure rests on. The infinitive form of elevation is to elevate.

Exterior: As used in this disclosure, the exterior is used as a relational term that implies that an object is not contained within the boundary of a structure or a space.

Fastener: As used in this disclosure, a fastener is a device that is used to join or affix two objects. Fasteners generally comprise a first element which is attached to the first object and a second element which is attached to the second object such that the first element and the second element join to removably attach the first object and the second object. Common fasteners include, but are not limited to, hooks, zippers, magnets, snaps, buttons, buckles, quick release buckles, or hook and loop fasteners. A fastener is often referred to as a fastening device.

Fitted: As used in this disclosure, the term fitted refers to two geometrically similar structures wherein the smaller geometrically similar structure inserts into the larger geometrically similar structure with a tight fit.

Force of Gravity: As used in this disclosure, the force of gravity refers to a vector that indicates the direction of the pull of gravity on an object at or near the surface of the earth.

Friction: As used in this disclosure, friction refers to a force that occurs between two objects that are in relative motion while in contact with each other. The force resists the relative motion of the two objects. More technically, friction refers to an exchange of energy between two objects that are in contact with each other that converts the energy of a directed relative motion between the two objects into randomly directed motions of the molecules that form both objects.

Garment: As used in this disclosure, a garment is a textile based structure that is used to cover an individual. Clothes, clothing, and apparel are synonyms for garment.

Hip: As used in this disclosure, the hip refers to the joint that attaches the thigh bone to the pelvis. The also refers to the region of the body surrounding the hip especially in the regions that are lateral relative to the hip.

Horizontal: As used in this disclosure, horizontal is a directional term that refers to a direction that is either: 1) parallel to the horizon; 2) perpendicular to the local force of gravity, or, 3) parallel to a supporting surface. In cases where the appropriate definition or definitions are not obvious, the second option should be used in interpreting the specification. Unless specifically noted in this disclosure, the horizontal direction is always perpendicular to the vertical direction.

Inferior: As used in this disclosure, the term inferior refers to a directional reference that is parallel to and in the same direction as the force of gravity when an object is positioned or used normally.

Interior: As used in this disclosure, the interior is used as a relational term that implies that an object is contained within the boundary of a structure or a space.

Inertia: As used in this disclosure, the term inertia describes an object that is not under the influence of an accelerating force. By not under the influence is meant that the velocity of the object maintains a constant speed and direction (i.e. the object is not under acceleration or deceleration).

Inertial Sensor: As used in this disclosure, an inertial sensor is a form of a force sensor that measures the change in the inertia of an object.

Load: As used in this disclosure, the term load refers to an object upon which a force is acting or which is otherwise absorbing energy in some fashion. Examples of a load in this sense include, but are not limited to, a mass that is being moved a distance or an electrical circuit element that draws energy. The term load is also commonly used to refer to the forces that are applied to a stationary structure.

Load Path: As used in this disclosure, a load path refers to a chain of one or more structures that transfers a load generated by a raised structure or object to a foundation, supporting surface, or the earth.

Logic Module: As used in this disclosure, a logic module is a readily and commercially available electrical device that accepts digital and analog inputs, processes the digital and analog inputs according to previously specified logical processes and provides the results of these previously specified logical processes as digital or analog outputs. The disclosure allows, but does not assume, that the logic module is programmable.

Modulus: As used in this disclosure, the modulus of an elastic textile or elastic sheeting is a function that describes the percentage change in the span of the elastic textile or elastic sheeting as a function of the force applied to the elastic textile or elastic sheeting. When comparing modulus, a larger modulus is taken to imply that an increase in force is required to get the same percentage change in the elastic textile or elastic sheeting.

Momentum: As used in this disclosure, momentum is a measured quantity associated with the mass of a moving object. The momentum of the object equals the mass of the object multiplied by the velocity of the object. The exchange of momentum between two objects is a conserved quantity meaning that the sum of the momentums of the two objects before an exchange of momentum equals the sum of the momentums of the two objects after the exchange.

Momentum Sensor: As used in this disclosure, a momentum sensor is a sensor that detects changes in the momentum of an object. The momentum sensor generates one or more electric signals that indicate: a) the magnitude of the change of momentum; and, b) the direction of the change of momentum.

Patient: As used in this disclosure, a patient is a person who is designated to receive a medical treatment, therapy, or service. The term patient may be extended to an animal when used within the context of the animal receiving veterinary treatment or services.

PDD: As used in this disclosure, PDD is an acronym for personal data device.

Personal Data Device: As used in this disclosure, a personal data device is a handheld logical device that is used for managing personal information and communication. Examples of personal data device include, but are not limited to, cellular phones, tablets, and smartphones.

Pelvis: As used in this disclosure, the pelvis refers to a bone structure near the base of the spine to which buttocks and the legs are joined. As used in this disclosure, the term pelvis is a more generally expanded to describe the above described region of the body. As used in this disclosure, the adjectival form of pelvis is pelvic.

Pocket: As used in this disclosure, a pocket is a small pouch or storage space that is formed on or into an object. Pockets are often formed by joining a second textile or a second sheeting to a first textile or a first sheeting, respectively, by sewing or heat sealing respectively. Methods to form pockets are well-known and documented in the textile and apparel arts.

Posterior: As used in this disclosure, posterior is a term that is used to refer to the side of an object that is distal or in the opposite direction of the anterior side. When comparing two items, the posterior item is the item that is distal from the anterior of the object.

Relaxed Shape: As used in this disclosure, a structure is considered to be in its relaxed state when no shear, strain, or torsional forces are being applied to the structure.

Sensor: As used in this disclosure, a sensor is a device that receives and responds in a predetermined way to a signal or stimulus. As further used in this disclosure, a threshold sensor is a sensor that generates a signal that indicates whether the signal or stimulus is above or below a given threshold for the signal or stimulus.

Sheeting: As used in this disclosure, a sheeting is a material, such as a paper, textile, a plastic, or a metal foil, in the form of a thin flexible layer or layers. The sheeting forms a disk structure. The two surfaces of the sheeting with the greatest surface area are called the faces of the sheeting.

Sleeve: As used in this disclosure, a sleeve is a tube like covering that is placed over an object.

Spine: As used in this disclosure, the spine of a human being comprises thirty-three individual bones that are formed in a column structure. The spine commonly referred to as the back bone. The spine is divided into five regions which are, in order from head to buttocks, the cervical region, the thoracic region, the lumbar region, the sacral region, and the coccyx region.

Superior: As used in this disclosure, the term superior refers to a directional reference that is parallel to and in the opposite direction of the force of gravity when an object is positioned or used normally.

Supporting Surface: As used in this disclosure, a supporting surface is a horizontal surface upon which an object is placed and to which the load of the object is transferred. This disclosure assumes that an object placed on the supporting surface is in an orientation that is appropriate for the normal or anticipated use of the object.

Textile: As used in this disclosure, a textile is a material that is woven, knitted, braided or felted. Synonyms in common usage for this definition include fabric and cloth. The two surfaces of the textile with the greatest surface area are called the faces of the textile.

Therapeutic: As used in this disclosure, therapeutic is an adjective that refers to a medical, ameliorative, or hygienic substance, process, procedure, or device.

Tight Fit: As used in this disclosure, a tight fit refers to the insertion of a first object into a second object such that there is not a lot of space between the first object and the second object. By not a lot of space is meant that friction occurs when the first object moves within the second object.

Torso: As used in this disclosure, the torso refers to the portion of a human body between the neck and the pelvis. The spine is primarily contained within the torso.

Vertical: As used in this disclosure, vertical refers to a direction that is either: 1) perpendicular to the horizontal direction; 2) parallel to the local force of gravity; or, 3) when referring to an individual object the direction from the designated top of the individual object to the designated bottom of the individual object. In cases where the appropriate definition or definitions are not obvious, the second option should be used in interpreting the specification. Unless specifically noted in this disclosure, the vertical direction is always perpendicular to the horizontal direction.

Waist: As used in this disclosure, the waist refers to the perimeter around the abdomen of a person. Traditionally, the perimeter formed by the waist is closer to the hips than the ribs of the person.

Wear: As used in this disclosure, the verb to wear means to secure a second object to a first object such that the second object covers the exterior surface of the first object. The verb to wear is often used in situations where the first object is a person and the second garment is a client. The adjective form of to wear is worn.

WiFi™: As used in this disclosure, WiFi™ refers to the physical implementation of a collection of wireless electronic communication standards commonly referred to as IEEE 802.11x.

Wireless: As used in this disclosure, wireless is an adjective that is used to describe a communication link between two devices that does not require the use of physical cabling.

Wireless Communication Link: As used in this disclosure, a wireless communication link is a previously determined channel that is used to wirelessly exchange information between one or more transceivers.

Wireless Communication Establishment Technology: As used in this disclosure, a wireless communication establishment technology refers to technology that establishes a wireless communication link between a first logical device and a second logical device. Usually, the operation of a wireless communication establishment technology is initiated by the push of a button. An example of such a technology is the WiFi™ protected setup technology (WPS™).

Zipper: As used in this disclosure, a zipper is a fastening device comprising a first chain tape, a second chain tape, and a zipper pull. The first chain tape and the second chain tape are textile webbings formed with interlocking components that form a chain. The chain is opened and closed by pulling a slide, called a zipper pull, over the first chain tape and the second chain tape. The individual elements of the chain are called the teeth of the chain.

With respect to the above description, it is to be realized that the optimum dimensional relationship for the various components of the invention described above and in FIGS. 1 through 5 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:

1. A motion-sensing garment comprising
a therapeutic structure;
wherein the therapeutic structure is a garment;
wherein the therapeutic structure is adapted for use with a patient;
wherein the therapeutic structure is adapted to be worn by the patient;
wherein the motion-sensing garment is adapted to monitor a motion of the patient during exercise;
wherein the motion-sensing garment is adapted to analyze a movement of the patient;
wherein the therapeutic structure is adapted to form a tight fit on the patient;
wherein the therapeutic structure is adapted to sense a change in a position of the patient;
wherein the therapeutic structure is adapted to measure a change of position of a specific location of the patient;
wherein the therapeutic structure analyzes the measured change of position of the specific location of a body of the patient;
wherein the therapeutic structure compares a change of a first measured location of the patient relative to a change of position of a second measured location of the patient to determine the motion of the first measured location relative to the second measured location.

2. The motion sensing garment according to claim 1
wherein the therapeutic structure analyzes the measured change of position of the first measured location of the patient to the second measured location of the patient;
wherein the therapeutic structure compares a relative change between two measured locations of the patient to determine a form the patient is using during the exercise;
wherein the therapeutic structure compares a measured exercise form of the patient to a form that is recommended for the exercise;
wherein the therapeutic structure provides a summary of a difference between the patient's exercise form and the recommended exercise form to the patient.

3. The motion sensing garment according to claim 2
wherein the therapeutic structure comprises a base garment, a base circuit, and a zippered pocket;
wherein the zippered pocket attaches to the base garment;
wherein the zippered pocket contains a portion of the base circuit.

4. The motion sensing garment according to claim 3
wherein the base garment forms the garment that is worn by the patient;
wherein the base garment is a compression garment.

5. The motion sensing garment according to claim 4
wherein the zippered pocket is a pocket that is formed on an exterior surface of the base garment that is worn by the patient;
wherein the zippered pocket further comprises a zipper;
wherein the zipper of the zippered pocket encloses the portion of the base circuit stored in the zippered pocket.

6. The motion sensing garment according to claim 5
wherein the base circuit is an electric circuit;
wherein the base circuit senses changes in the position of the patient;

wherein the base circuit measures the change of position of the one or more specific locations of the patient;

wherein the base circuit measures the change of position of the one or more specific locations of the patient while the patient is exercising;

wherein the base circuit analyzes the measured change of position of each measured location of the body of the patient;

wherein the base circuit compares the change of any first measured location of the patient relative to the change of position of any second measured location of the patient to determine the motion of the first measured location relative to the second measured location;

wherein the base circuit analyzes the measured change of position of any measured first location of the patient to the measured position of each of the other measured locations of the patient;

wherein the base circuit compares the relative change between any two measured locations of the patient to determine the form the patient is using during the exercise;

wherein the base circuit compares the measured exercise form of the patient to the form that is recommended for the exercise;

wherein the base circuit provides the summary of the differences between the patient's exercise form and the recommended exercise form to the patient.

7. The motion sensing garment according to claim 6 wherein the base circuit comprises a communication module, a plurality of inertial sensors, and a personal data device;

wherein the communication module, and the plurality of inertial sensors are electrically interconnected;

wherein the communication module forms a communication link with the personal data device.

8. The motion sensing garment according to claim 7 wherein the personal data device is a programmable electrical device;

wherein the personal data device further comprises an application;

wherein the application of the personal data device forms an interface between the base circuit and the patient using the motion-sensing garment;

wherein the personal data device transmits operating instructions over the wireless communication link to the base circuit;

wherein the communication module receives the transmitted operating instructions.

9. The motion sensing garment according to claim 8 wherein each inertial sensor selected from the plurality of inertial sensors is a sensor that is mounted on the base garment;

wherein the compression provided by the base garment configured to maintain each selected inertial sensor in a fixed position relative to the patient;

wherein each selected inertial sensor senses changes in the position of the selected inertial sensor relative to a force of gravity;

wherein each selected inertial sensor converts the sensed change of position into an electric signal;

wherein each selected inertial sensor transmits the converted electric signal to the logic module for further processing.

10. The motion sensing garment according to claim 9 wherein the application compares the received relative motions between the plurality of inertial sensors against the motions recommended for each exercise;

wherein the application provides the summary of the differences between the patient's exercise form and the recommended exercise form to the patient through the personal data device.

11. The motion sensing garment according to claim 10 wherein the therapeutic structure comprises a superior therapeutic structure;

wherein the superior therapeutic structure is an instantiation of the motion-sensing garment;

wherein the superior therapeutic structure is configured to be worn by the patient while exercising;

wherein the superior therapeutic structure is configured to enclose the torso and arms of the patient.

12. The motion sensing garment according to claim 10 wherein the therapeutic structure comprises an inferior therapeutic structure;

wherein the inferior therapeutic structure is an instantiation of the motion-sensing garment;

wherein the inferior therapeutic structure is configured to be worn by the patient while exercising;

wherein the inferior therapeutic structure is configured to enclose the hips, pelvis, and legs of the patient.

* * * * *